US009808264B2

(12) United States Patent
Estes et al.

(10) Patent No.: US 9,808,264 B2
(45) Date of Patent: Nov. 7, 2017

(54) HINGED MICROFRACTURE AWLS

(71) Applicants: THE UAB RESEARCH FOUNDATION, Birmingham, AL (US); SOUTHERN RESEARCH INSTITUTE, Birmingham, AL (US)

(72) Inventors: Reed Estes, Birmingham, AL (US); Patrick Schexnailder, Birmingham, AL (US); Robert Hergenrother, Birmingham, AL (US)

(73) Assignees: THE UAB RESEARCH FOUNDATION, Birmingham, AL (US); SOUTHERN RESEARCH INSTITUTE, Birmingham, AL (US)

( * ) Notice: Subject to any disclaimer, the term of this patent is extended or adjusted under 35 U.S.C. 154(b) by 0 days.

(21) Appl. No.: 15/311,558

(22) PCT Filed: May 21, 2015

(86) PCT No.: PCT/US2015/031983
§ 371 (c)(1),
(2) Date: Nov. 16, 2016

(87) PCT Pub. No.: WO2015/179646
PCT Pub. Date: Nov. 26, 2015

(65) Prior Publication Data
US 2017/0079667 A1 Mar. 23, 2017

Related U.S. Application Data

(60) Provisional application No. 62/001,317, filed on May 21, 2014.

(51) Int. Cl.
*A61B 17/00* (2006.01)
*A61B 17/16* (2006.01)
*A61B 90/00* (2016.01)

(52) U.S. Cl.
CPC ...... *A61B 17/1657* (2013.01); *A61B 17/1604* (2013.01); *A61B 17/1631* (2013.01); *A61B 2090/034* (2016.02)

(58) Field of Classification Search
CPC combination set(s) only.
See application file for complete search history.

(56) References Cited

U.S. PATENT DOCUMENTS 115,289 A 5/1871 Evans
518,600 A 4/1894 Hallman
(Continued)

FOREIGN PATENT DOCUMENTS

EP 2236100 A1 10/2010
EP 2459082 A1 6/2012
(Continued)

OTHER PUBLICATIONS

International Search Report for PCT/US2015/031983 dated Aug. 17, 2015.

*Primary Examiner* — Sameh Boles
(74) *Attorney, Agent, or Firm* — Thomas | Horstemeyer, LLP

(57) ABSTRACT

In one embodiment, a hinged microfracture awl includes a handle, and a shaft that extends through and from the handle, the shaft being pivotally mounted to the handle with a hinge, wherein a distal end of the shaft includes a sharp tip adapted to pierce bone and a proximal end of the shaft includes an impact head adapted to be struck by a striking tool.

16 Claims, 5 Drawing Sheets

(56) References Cited

U.S. PATENT DOCUMENTS

| | | |
|---|---|---|
| 6,436,122 B1 | 8/2002 | Frank et al. |
| 6,960,214 B2 | 11/2005 | Burkinshaw |
| 8,251,998 B2 | 8/2012 | Hoeppner et al. |
| 2007/0123889 A1 | 5/2007 | Malandain et al. |
| 2010/0076440 A1 | 3/2010 | Pamichev et al. |
| 2011/0319895 A1 | 12/2011 | Gamache |
| 2012/0071876 A1 | 3/2012 | Stoll et al. |
| 2012/0232556 A1 | 9/2012 | Frederic et al. |
| 2014/0155896 A1 | 6/2014 | Cournoyer et al. |
| 2014/0214039 A1 | 7/2014 | Hernandez et al. |

FOREIGN PATENT DOCUMENTS

| | | |
|---|---|---|
| WO | 2010148125 A1 | 12/2010 |
| WO | 2013112308 A1 | 8/2013 |

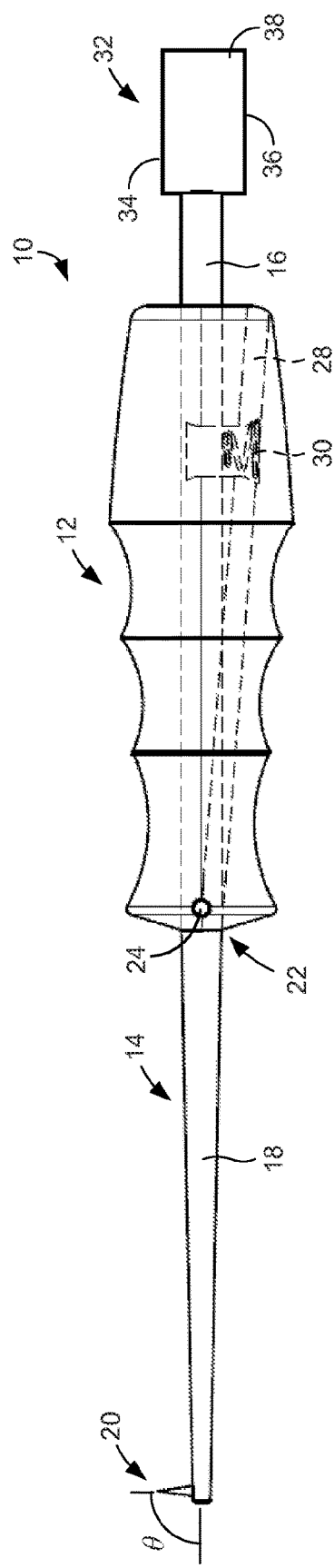
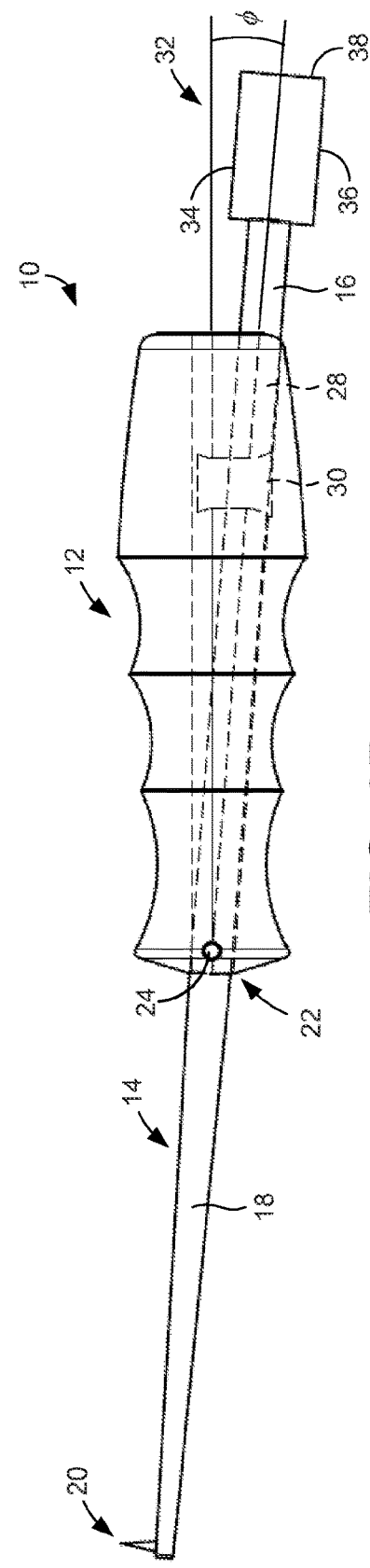
FIG. 2A
FIG. 2B

HINGED MICROFRACTURE AWLS

CROSS-REFERENCE TO RELATED APPLICATION

This application is the 35 U.S.C. §371 National Stage application of PCT Application No. PCT/US2015/031983, filed May 21, 2015, where the PCT claims priority to U.S. Provisional Application Ser. No. 62/001,317, filed May 21, 2014, both of which are hereby incorporated by reference herein in their entireties.

BACKGROUND

Microfracture procedures are used to improve the feasibility of cartilage restoration. The goal of a microfracture procedure is to produce in a controlled fashion small fractures within the bone underlying a cartilage deficit. Bone marrow is stimulated through creation of such fractures, which promotes the release of healing cells and signals molecules that improve and direct cartilage growth.

Microfracturing is typically performed using a microfracture awl, which normally comprises an elongated spike that extends from a handle in similar manner to a scratch awl used in woodworking. The sharp tip of the spike is axially driven into the bone by hammering the proximal end of the handle in the longitudinal direction of the spike. While such awls can be useful, the shearing forces generated when driving such an awl create the opportunity for unintended cartilage damage. It can therefore be appreciated that it would be desirable to have an alternative microfracture awl for microfracture procedures.

BRIEF DESCRIPTION OF THE DRAWINGS

The present disclosure may be better understood with reference to the following figures. Matching reference numerals designate corresponding parts throughout the figures, which are not necessarily drawn to scale.

FIG. 2A is a first side view of the awl of FIG. 1, illustrating an initial orientation of a shaft of the awl.

FIG. 2B is a second side view of the awl of FIG. 1, illustrating a pivoted orientation of the shaft of the awl.

DETAILED DESCRIPTION

As described above, the use of conventional microfracture awls can result in unintended cartilage damage. Disclosed herein are alternative microfracture awls that reduce the likelihood for such damage. The disclosed awls comprise a shaft that extends through and from a handle. Provided at a distal end of the shaft is an angled tip that is adapted to pierce bone. Provided at a proximal end of the shaft is an impact head that is adapted to be struck in a direction that is generally perpendicular to the longitudinal axis of the shaft. The approximate midpoint of the shaft is pivotally mounted to the handle with a hinge such that, when the impact head is struck, the shaft is pivoted and the shaft tip moves in an opposite direction.

In the following disclosure, various specific embodiments are described. It is to be understood that those embodiments are example implementations of the disclosed inventions and that alternative embodiments are possible. All such embodiments are intended to fall within the scope of this disclosure.

Figure 1:
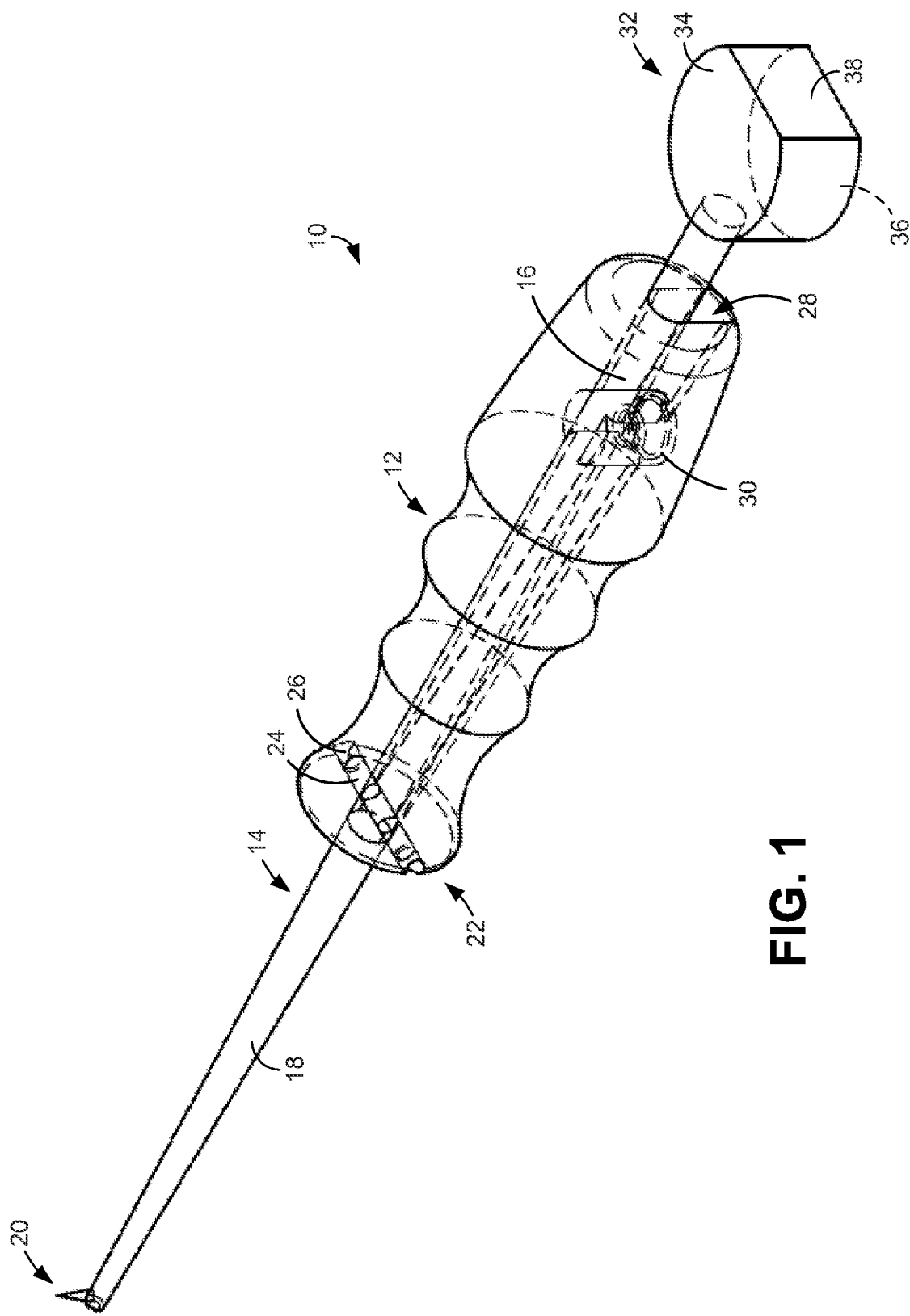
FIG. 1 is a top perspective view of a first embodiment of a hinged microfracture awl.

FIGS. 1 and 2 illustrate an embodiment of a hinged microfracture awl 10. As shown in the figure, the awl 10 generally includes a handle 12 and an elongated shaft 14 that extends from and through the handle. The handle 12 is generally cylindrical and sized and shaped for gripping with one hand during a microfracture procedure. In some embodiments, the handle 12 is ergonomically designed so as to have a contoured grip adapted to receive the user's fingers. In some embodiments, the handle 12 can be made of a metal (e.g., stainless steel or aluminum), polymeric, or rubber material.

The shaft 14 can be made of a biocompatible metal material, such as stainless steel. The shaft 14 includes a proximal portion 16 that extends through the handle 12 and a distal portion 18 that extends outward from a distal end of the handle. Provided at a distal end of the distal portion 18 of the shaft 14 is a sharp tip 20 that is adapted to penetrate bone. The tip 20 is a small fraction of the length of the distal portion 18 of the shaft 14 and is tapered. As is apparent from FIG. 2A, the tip 20 forms an angle θ with the longitudinal axis of the shaft 14. In some embodiments, the angle is approximately 90 degrees. In other embodiments, however, the tip 20 can form an acute angle with the longitudinal axis of the shaft 14. For example, the tip can form an angle θ of approximately 10 to 80 degrees with the longitudinal axis of the shaft 14 so as to extend both upward and outward from the distal end of the distal portion 18 of the shaft.

The shaft 14 is pivotally mounted at its approximate midpoint to the handle 12 with a hinge 22 that acts as a fulcrum for the shaft. In the illustrated embodiment, the hinge 22 is formed by a transverse cylindrical pivot rod 24 of the shaft 14 that is positioned approximately halfway along the length of the shaft and a transverse bore 26 of the handle 12 located near its distal end in which the rod is received and can rotate.

The proximal portion 16 of the shaft 14 extends through an elongated passage 28 of the handle 12 that generally extends along the longitudinal axis of the handle from its proximal end to its distal end. As is apparent in FIGS. 1 and 2, the passage 28 is tall enough to enable the shaft 14 to pivot from an initial orientation in which its longitudinal axis is generally coincident with the longitudinal axis of the handle 12 (FIG. 2A) to a pivoted orientation in which the shaft's longitudinal axis forms an acute angle φ with the handle's longitudinal axis (FIG. 2B). In some embodiments, this can be achieved by forming the passage 28 to have a base that diverges from the longitudinal axis of the handle 12 as the handle is traversed from its distal end to its proximal end. In some embodiments, the shaft 14 can be pivoted through and angle φ approximately 5 to 10 degrees from the longitudinal axis of the handle 12.

With further reference to FIGS. 1 and 2, a biasing element 30 is provided within the handle 12 below the shaft 14 near the handle's proximal end. In some embodiments, the biasing element 30 comprises a compression spring that generally opposes downward pivoting of the shaft 14 and maintains the shaft in the initial orientation shown in FIG. 2A when no external forces are acting upon the shaft (other than gravity). In other embodiments, the biasing element 30 can comprise a resilient pad.

Positioned at a proximal end of the shaft 14 is an impact head 32 that can be struck with a mallet or other striking tool to drive the tip 20 of the shaft into bone. As is apparent in FIGS. 1 and 2, the impact head 32 includes a first or top striking surface 34 and an opposed second or bottom striking surface 36 that can be struck by the striking tool. Each striking surface 34, 36 is generally planar parallel with the longitudinal axis of the shaft 14. Accordingly, the striking surfaces 34, 36 are adapted to be struck in a direction that is generally perpendicular to the longitudinal axis of the shaft 14 (and the handle 12 when the shaft is in the initial orientation of FIG. 2A). When the sharp tip 20 is perpendicular to the shaft 14 as shown in the figures, a striking force imparted to one of the striking surfaces 34, 36 causes the shaft 14 to pivot about the hinge 22.

FIGS. 2A and 2B illustrate pivoting of the shaft 12 in response to a downward blow imparted to the top striking surface 34. In FIG. 2A, the shaft 14 is shown in the initial orientation prior to the impact head 32 being struck. As is apparent from this figure, the biasing element 30 maintains the shaft 14 in an orientation in which the shaft's longitudinal axis is generally coincident with the longitudinal axis of the handle 12. Once the striking surface 34 is struck with a downward blow, however, the shaft 14 pivots about the hinge 22, the impact head 32 is displaced downward against the force of the biasing element 30, and the sharp tip 20 is driven upward, as shown in FIG. 2B. The sharp tip 20 can be driven into bone in this matter during a microfracture procedure. Because of this upward displacement of the sharp 20, as opposed to the axial displacement achieved using conventional awls, the shearing forces typically encountered with conventional microfracture procedures are not imparted to the bone. After the blow has been delivered and no further force acts upon the impact head 32, the shaft 14 can be returned to the initial orientation of FIG. 2A under the force of the biasing element 30.

With further reference to FIGS. 1 and 2, the impact head 32 can also include a third or end striking surface 38 that can be used to deliver forces along the longitudinal axis of the shaft 14, if desired. This may be desirable in situations in which the sharp tip 20 is angled forward from the distal end of the shaft 14.

Figure 3:
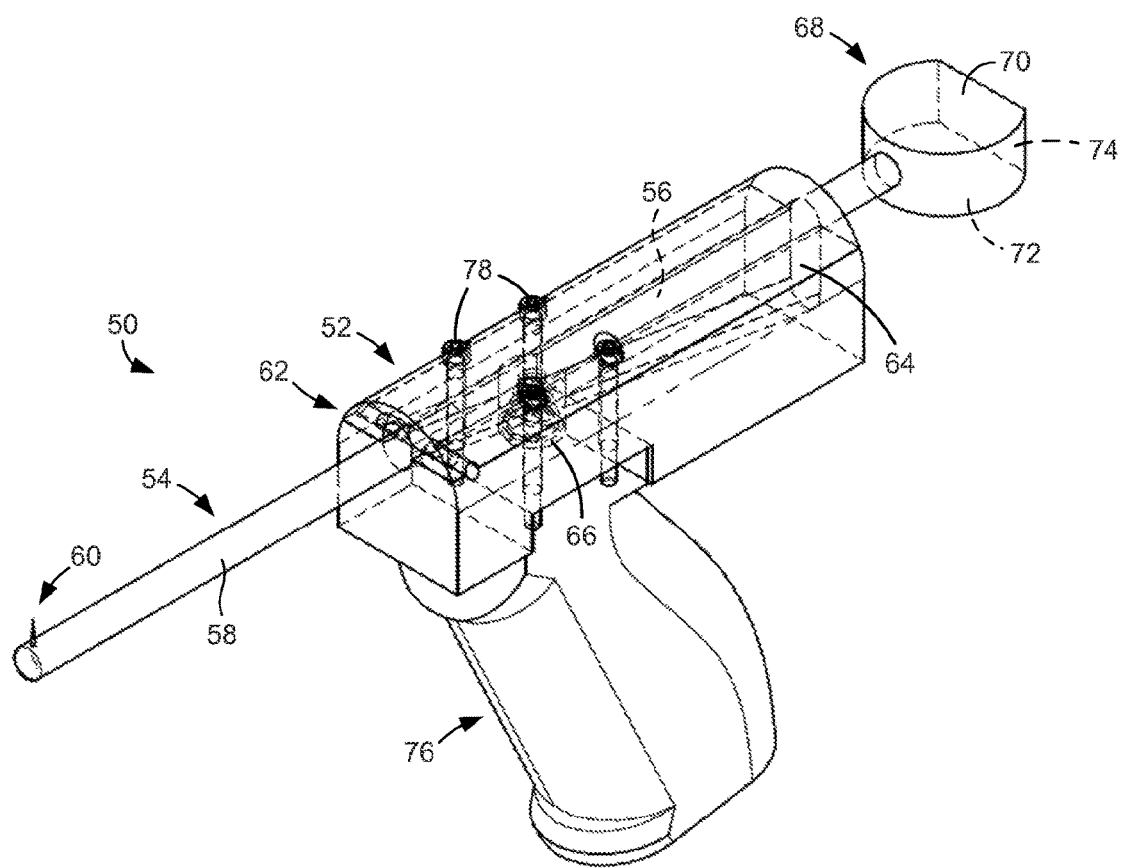
FIG. 3 is a top perspective view of a second embodiment of a hinged microfracture awl.
Figure 4A:
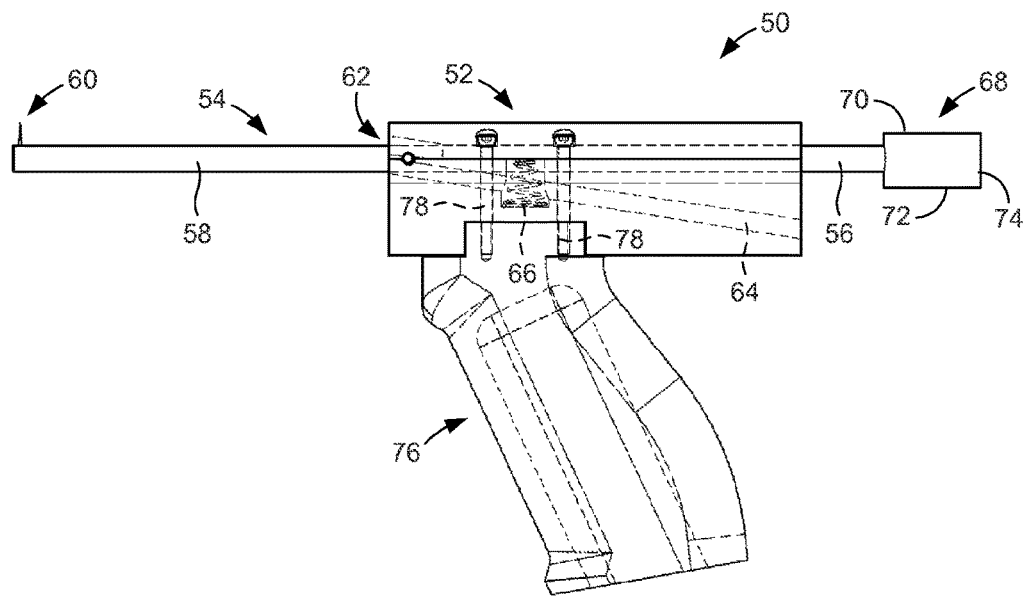
FIG. 4A is a first side view of the awl of FIG. 3, illustrating an initial orientation of a shaft of the awl.
Figure 4B:
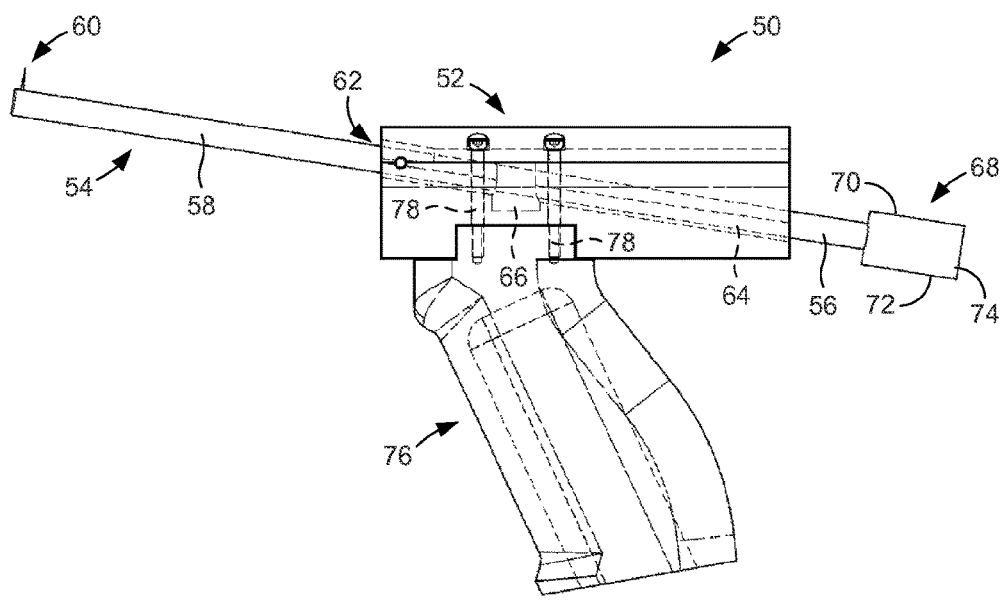
FIG. 4B is a second side view of the awl of FIG. 3, illustrating a pivoted orientation of the shaft of the awl.

FIGS. 3 and 4 illustrate a second embodiment of a hinged microfracture awl 50 that is similar in several ways to the awl 10 shown in FIGS. 1 and 2. Accordingly, the awl 50 generally includes a handle 52 and an elongated shaft 54. The shaft 54 includes a proximal portion 56 that extends through the handle 52 and a distal portion 58 that extends outward from a distal end of the handle. Provided at a distal end of the distal portion 58 of the shaft 54 is a sharp tip 60 that is adapted to penetrate bone. The shaft 54 is pivotally mounted at its approximate midpoint to the handle 52 with a hinge 62 that acts as a fulcrum for the shaft. The proximal portion 56 of the shaft 54 extends through an elongated passage 64 of the handle 52 that generally extends along the longitudinal axis of the handle from its proximal end to its distal end. With further reference to FIGS. 3 and 4, a biasing element 66 is provided within the handle 52 below the shaft 54 near the handle's distal end that generally opposes downward pivoting of the shaft and maintains the shaft in the initial orientation shown in FIG. 4A. Positioned at a proximal end of the shaft 54 is an impact head 68 that includes a first or top striking surface 70, and an opposed second or bottom striking surface 72, and a third or end striking surface 74 that can be struck by the mallet or other striking tool.

Unlike the awl 10 of FIGS. 1 and 2, however, the handle 52 of microfracture awl 50 includes a pistol grip portion 76 that extends downward from the top portion of the handle (or the upper, portion or "body" of the handle) and is configured like a grip of a handgun and therefore can be gripped as such. Such a grip may be more stable and may be preferred by some surgeons. As shown in FIGS. 3 and 4, the pistol grip portion 76 can be secured to the top portion of the handle 52 with multiple threaded fasteners 78. Notably, the orientation of the pistol grip portion 76 can be rotated in 90 degree increments relative to the top portion of the handle 52 by loosening and removing the fasteners 78, reorienting the pistol grip portion 76, and reinserting and retightening the fasteners. It is also noted that, in both embodiments, the direction the sharp tip 20, 60 is facing (i.e., upward or downward) can be altered by inverting the shaft 14, 54.

Figure 5:
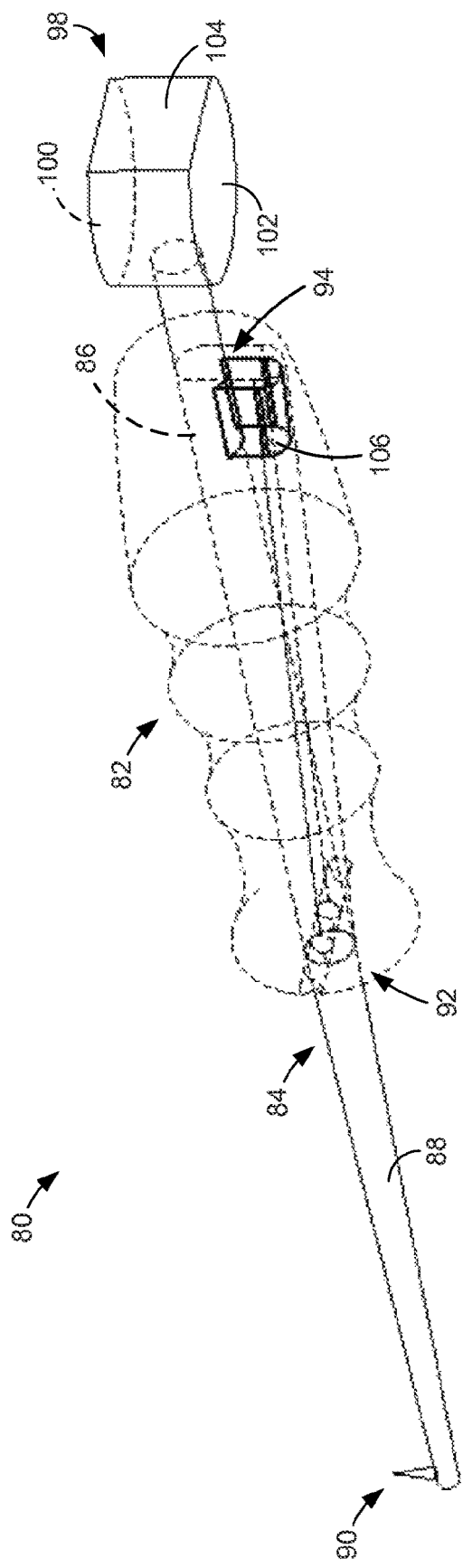
FIG. 5 is a bottom perspective view of a third embodiment of a hinged microfracture awl.

FIG. 5 illustrates a third embodiment of a hinged microfracture awl 80 that is substantially identical to the awl 10 shown in FIG. 1. Accordingly, the awl 80 generally includes a handle 82 and an elongated shaft 84. The shaft 84 includes a proximal portion 86 that extends through the handle 82 and a distal portion 88 that extends outward from a distal end of the handle. Provided at a distal end of the distal portion 88 of the shaft 84 is a sharp tip 90 that is adapted to penetrate bone. The shaft 84 is pivotally mounted at its approximate midpoint to the handle 82 with a hinge 92 that acts as a fulcrum for the shaft. The proximal portion 86 of the shaft 84 extends through an elongated passage 94 of the handle 82 that generally extends along the longitudinal axis of the handle from its proximal end to its distal end. A biasing element (not shown) can be provided within the handle 82 below the shaft 84 to oppose downward pivoting of the shaft. Positioned at a proximal end of the shaft 84 is an impact head 98 that includes a first or top striking surface 100, and an opposed second or bottom striking surface 102, and a third or end striking surface 104 that can be struck by the mallet or other striking tool.

Also included in the embodiment of FIG. 5, however, is a removable stop 106 that is positioned beneath the shaft 84 within the passage 94. Like the handle 82, the stop 106 can be made of a metal, polymeric, or rubber material. When positioned within the passage 94, the stop 106 limits pivoting of the shaft 84. Depending upon its height, the stop 106 can completely prevent the shaft 84 from pivoting relative to the handle 82 or merely limit the angle through which the shaft pivots relative to the handle. In the latter case, the height of the stop 106 can be selected to effect the angle, and the depth to which the sharp tip 90 penetrates bone. Notably, a stop similar to the stop 106 can be used with hinged microfracture awl embodiments that include a pistol grip, such as the embodiment shown in FIGS. 3 and 4. In addition, the stop could be adjustable in height, in which case it may not need to be removable.

The invention claimed is:

1. A hinged microfracture awl comprising:
a handle; and
a shaft that extends through and from the handle, the shaft being pivotally mounted to the handle with a hinge, wherein a distal end of the shaft includes a sharp tip adapted to pierce bone and a proximal end of the shaft includes an impact head adapted to be struck by a striking tool.

2. The awl of claim 1, wherein the shaft can pivot several degrees relative to the handle so as to drive the sharp tip into bone.

3. The awl of claim 1, wherein the handle is generally cylindrical.

4. The awl of claim 3, wherein the handle has a contoured grip adapted to receive a user's fingers.

5. The awl of claim 1, wherein the handle includes a pistol grip portion that extends downward from a remainder of the handle.

6. The awl of claim 5, wherein the pistol grip portion has a contoured grip adapted to receive a user's fingers.

7. The awl of claim 1, wherein the handle includes an elongated passage through which the shaft extends, the passage extending from a distal end of the handle to a proximal end of the handle.

8. The awl of claim 1, wherein the hinge comprises a transverse rod of the shaft and a transverse bore of the handle in which the rod is received and can rotate.

9. The awl of claim 1, wherein the sharp tip forms an angle of approximately 90° with a longitudinal axis of the shaft.

10. The awl of claim 1, wherein the sharp tip forms an acute angle with a longitudinal axis of the shaft.

11. The awl of claim 1, wherein the impact head includes a generally planar top striking surface adapted to be struck by a striking tool.

12. The awl of claim 11, wherein the top striking surface is generally parallel with a longitudinal axis of the shaft.

13. The awl of claim 12, wherein the impact head also includes a generally planar end striking surface that is generally perpendicular to the longitudinal axis of the shaft.

14. The awl of claim 1, wherein the handle further comprises an inner biasing element that returns the shaft to an initial orientation in which a longitudinal axis of the shaft is generally coincident with a longitudinal axis of the handle after the impact head has been struck.

15. The awl of claim 1, further comprising a stop that limits pivoting of the shaft relative to the handle.

16. The awl of claim 15, wherein the stop fits within the handle.

\* \* \* \* \*